US006214351B1

(12) United States Patent
Wadsworth et al.

(10) Patent No.: US 6,214,351 B1
(45) Date of Patent: Apr. 10, 2001

(54) MORINDA CITRIFOLIA OIL

(75) Inventors: John J. Wadsworth, Orem; Stephen P. Story, Alpine, both of UT (US)

(73) Assignee: Morinda, Inc., Provo, UT (US)

( * ) Notice: Subject to any disclaimer, the term of this patent is extended or adjusted under 35 U.S.C. 154(b) by 0 days.

(21) Appl. No.: 09/384,785

(22) Filed: Aug. 27, 1999

(51) Int. Cl.[7] .................................................. A01N 65/00
(52) U.S. Cl. .......................................................... 424/195.1
(58) Field of Search ......................................... 424/195.1

(56) References Cited

U.S. PATENT DOCUMENTS

| | | | |
|---|---|---|---|
| 4,409,144 | 10/1983 | Heinicke | 260/236 |
| 4,543,212 | 9/1985 | Heinicke | 546/1 |
| 4,666,606 | 5/1987 | Heinicke | 210/632 |
| 4,948,785 | 8/1990 | Nguyen | 514/54 |
| 5,110,803 | 5/1992 | Nguyen | 514/54 |
| 5,268,467 | 12/1993 | Verbiscar | 536/123 |
| 5,275,834 | 1/1994 | Thibault et al. | 426/577 |
| 5,288,491 | 2/1994 | Moniz | 424/195 |

*Primary Examiner*—Herbert J. Lilling
(74) *Attorney, Agent, or Firm*—Madson & Metcalf

(57) ABSTRACT

An essential oil product obtained from the Indian mulberry (*Morinda citrifolia*) plant and the process of extracting and purifying the oil is disclosed. According to one embodiment, the seeds from the Indian mulberry fruit are dried, preferably to a moisture content less than 10%. The seeds are ground or shredded to facilitate the removal of natural occurring oil. The shredded or ground flakes are pressed to expel *Morinda citrifolia* oil. The remaining seed cake is then mixed with a food grade, non-polar extraction solvent such as hexane. The mixture is heated for a sufficient length of time to complete the extraction process. The extraction solvent is then evaporated from the mixture leaving the *Morinda citrifolia* oil. The oil is further refined, bleached, dried, and deodorized to remove free fatty acids and other unwanted components. An antioxidant can optionally be added to stabilize the oil for further processing or packaging.

24 Claims, No Drawings

MORINDA CITRIFOLIA OIL

FIELD OF THE INVENTION

The present invention relates an essential oil product obtained from the *Morinda citrifolia* plant and to the process of extracting and purifying the oil.

BACKGROUND OF INVENTION

The Indian Mulberry plant, known scientifically as *Morinda citrifolia* L., is a shrub, or small or medium sized tree 3 to 10 meters high. It grows in tropical coastal regions around the world. The plant grows randomly in the wild, and it has been cultivated in plantations and small individual growing plots. The Indian mulberry plant has somewhat rounded branches and evergreen, opposite (or spuriously alternate), dark, glossy, wavy, prominently-veined leaves. The leaves are broadly elliptic to oblong, pointed at both ends, 10–30 cm in length and 5–15 cm wide.

The Indian mulberry flowers are small, white, 3 to 5 lobed, tubular, fragrant, and about 1.25 cm long. The flowers develop into compound fruits composed of many small drupes fused into an ovoid, ellipsoid or roundish, lumpy body, 5–10 cm long, 5–7 cm thick, with waxy, white or greenish-white or yellowish, semi-translucent skin. The fruit contains "eyes" on its surface, similar to a potato. The fruit is juicy, bitter, dull-yellow or yellowish-white, and contains numerous red-brown, hard, oblong-triangular, winged, 2-celled stones, each containing 4 seeds.

When fully ripe, the fruit has a pronounced odor like rancid cheese. Although the fruit has been eaten by several nationalities as food, the most common use of the Indian mulberry plant was as a red and yellow dye source. Recently, there has been an interest in the nutritional and health benefits of the Indian mulberry plant.

It would be a significant advancement in the art to provide the essential oil from the Indian mulberry plant and to provide a process for obtaining the essential oil from the Indian mulberry plant.

SUMMARY OF THE INVENTION

The present invention is directed to an essential oil extracted from Indian mulberry (*Morinda citrifolia*) seeds and to a process of extracting the oil. The Indian mulberry oil typically includes a mixture of several different fatty acids as triglycerides, such as palmitic, stearic, oleic, and linoleic fatty acids, and other fatty acids present in lesser quantities.

The essential oil preferably includes an antioxidant to inhibit spoilage of the oil. Conventional, food grade antioxidants are preferably used, including, but not limited to, tocopherol acetate (vitamin E acetate), propyl gallate, TBHQ (t-butyl hydroquinone), BHT (3,5-bis(t-butyl)-4-hydroxytoluene), and French maritime pine bark extract.

The process for extracting Indian mulberry oil from its seeds typically involves obtaining Indian mulberry seeds that are dried to a moisture content less than 10%, by weight, and preferably from 5% to 8%, by weight. The seeds are cracked, ground, or reduced in size, typically from 2 to 20 mm. The flaked seeds are then pressed in a mechanical press or screw press to expel some of the oil. The remaining seed cake is mixed with a nonpolar extraction solvent. The extraction solvent is preferable food-grade. One currently preferred nonpolar solvent is hexane.

Oil extraction with the nonpolar solvent preferably takes place at a temperature range between 80° F. and 200° F. and ranges from a time of 30 minutes up to 12 hours. It is presently preferred to complete the extraction step as quickly as possible. The nonpolar solvent is preferably removed from the extracted oil through flash evaporation.

The oil from the mechanical press and from the nonpolar solvent extraction may be combined or further refined separately. The refining process removes impurities from the oil. Caustic, water, and phosphoric acid can be added to the oil to precipitate impurities. The precipitating agents and oil are mixed and heated to a temperature between 100° F. and 200° F., the currently preferred target temperature is between 170° F. and 180° F. The mixture is centrifuged to remove precipitated impurities that include, but are not limited to, insoluble gums, phosphatides, and free fatty acids.

The oil can optionally be further refined by bleaching and deodorizing. Bleaching involves the addition of one or more filtering agents to the oil. The oil is filtered through a mechanical filter to remove the filtering agents. Currently preferred filtering agents include diatomaceous earth (D.E.) and activated charcoal. Bleaching removes color bodies and soap materials generated during the refining process. Bleaching is preferably done at temperatures between 100° F. and 200° F.

The oil may or may not be vacuumed dried to remove any residual water. The oil is deodorized to remove volatile impurities. This involves steam distillation under a vacuum and at temperatures between 300° F. and 500° F. An antioxidant can be included with the extracted oil, as mentioned above.

DETAILED DESCRIPTION OF THE INVENTION

The present invention is directed to an essential oil product obtained from the Indian mulberry (*Morinda citrifolia*) plant and to the process of extracting and purifying the oil. According to one currently preferred embodiment within the scope of the present invention, the oil is extracted from Indian mulberry seeds. The seeds from the Indian mulberry fruit are dried and then packed in large containers for storage and transport. The seeds can be processed immediately or they can be stored for a period of time, usually up to about one year.

The seeds are preferably dried because residual water can contaminate the extraction solvent, which is oil based. Also the presence of water in the extraction process can cause oxidation of the oil. The rate of drying is preferably quick enough to be economical and slow enough to protect the oil from heat degradation. Drying usually takes from 10 to 100 days. The seeds are preferably dried in the sun or by a mechanical drier. The seeds are preferably dried to a moisture content less than 10%, by weight, and more preferably from about 5% to 8%, by weight. Conventional moisture detectors can be used to measure the moisture content of the seeds during and after the drying process.

The seeds are cracked and ground or reduced in size to a flake in order to facilitate the removal of natural occurring oil. The seeds are preferably ground through a grinder or flaker with a grinder plate size between about 2 mm to 20 mm hole size. The seeds are optimally reduced to a size falling in this range. The ground seed size is important because it effects the yield and quality of the extracted oil. Too large a flake size decreases the yield. Too small a flake size leaves a lot of undesired seed components in the oil.

The cracked, flaked, or ground seeds are preferably pressed in a mechanical press or screw press to expel some of the oil. The remaining seed cake is mixed with a nonpolar, food grade extraction solvent. Hexane is a currently preferred nonpolar solvent. The mixture of nonpolar solvent and seed cake is preferably heated to a temperature between 80° F. and 200° F. and for a time from about 30 minutes up to 12 hours. The nonpolar solvent mixes with the Indian mulberry oil remaining in the seeds and carries the oil out of the water-based seed material matrix.

Indian mulberry oil pressed from the seeds and from the hexane extraction may be combined or further refined separately to remove impurities from the oil. Such unwanted impurities include, but are not limited to, insoluble gums, phosphatides, and free fatty acids. Caustic, water, and phosphoric acid are currently preferred precipitating agents that can be added to the oil to precipitate impurities. The oil and precipitating agent mixture is preferably heated to a temperature between 100° F. and 200° F., and more preferably heated to a temperature between 170° F. to 180° F. The mixture is preferably centrifuged to remove the precipitated impurities.

The oil may be optionally further refined by bleaching and deodorizing. Bleaching involves the addition of one or more filtering agents to the oil to remove color bodies and soap materials generated during the refining process.

Currently preferred filtering agents include, but are not limited to diatomaceous earth (D.E.) and activated charcoal. The oil is filtered through a mechanical filter to remove the filtering agents. Bleaching is done at temperatures between 100° F. and 200° F. Residual water can be removed from the oil by vacuum drying.

The oil is preferably deodorized to remove volatile impurities. This involves steam distillation under a vacuum. Typical distillation temperatures range from 300° F. and 500° F.

An antioxidant can optionally be added to stabilize the oil for further processing or packaging. Suitable antioxidants include, but are not limited to, tocopherol acetate (vitamin E acetate), propyl gallate, TBHQ (t-butyl hydroquinone), BHT (3,5-bis(t-butyl)-4-hydroxytoluene), French maritime pine bark extract. The *Morinda citrifolia* seed oil may be used in, but is not limited to massage oil, cosmetics, candles, and as a product by itself.

The fragrance of the oil ranges from a nutty, mellow fragrance to a slightly sharp chemical solvent fragrance. The extracted oil appearance is from a rich golden yellow to a brownish tan color with a clear transparency, preferably free of foreign material or particulates.

From an analysis of the *Morinda citrifolia* oil, the oil is mainly composed of fatty acids as triglycerides. The free fatty acid content typically ranges from 5 to 9 grams/100 grams oil. The peroxide value typically ranges from 3 to 6 MEQ/KG, and the vitamin E content typically ranges from 11 to 25 IU/100 gram. The approximate fatty acid composition of the oil is reported below in Table 1.

TABLE 1

| Fatty Acid | Wt. % |
| --- | --- |
| Caprylic | 0.5 |
| Palmitic | 8.4 |
| Stearic | 4.0 |
| Oleic | 13.8 |
| Linoleic | 66.8 |
| Linolenic | 0.2 |
| Arachidic | 0.5 |
| Eicosenoic | 0.2 |
| Other fatty acids | 5.6 |

The foregoing concentrations in the extracted oil can vary from one batch to another, but the variations generally do not exceed ±10%, by weight.

The present invention may be embodied in other specific forms without departing from its essential characteristics. The described embodiments are to be considered in all respects only as illustrative and not restrictive. The scope of the invention is, therefore, indicated by the appended claims rather than by the foregoing description.

The claimed invention is:

1. A process for extracting oil from *Morinda citrifolia* seeds comprising the steps of:

obtaining *Morinda citrifolia* seeds that are dried to a moisture content less than 10%;

processing the seeds by cracking, flaking, or grinding to reduce their size; and pressing the processed seeds to expel *Morinda citrifolia* oil.

2. A process for extracting oil from *Morinda citrifolia* seeds according to claim 1, further comprising the steps of:

mixing the pressed, processed seeds with a nonpolar extraction solvent to allow *Morinda citrifolia* oil from the seeds to mix with the extraction solvent; and heating the mixture of seeds and extraction solvent to a temperature from 80° F. and 200° F. to extract *Morinda citrifolia* oil from the seeds.

3. A process for extracting oil from *Morinda citrifolia* seeds according to claim 2, wherein the mixture is heated for a period between 30 minutes and 12 hours.

4. A process for extracting oil from *Morinda citrifolia* seeds according to claim 2, further comprising the step of removing the extraction solvent from the extracted *Morinda citrifolia* oil by evaporation.

5. A process for extracting oil from *Morinda citrifolia* seeds according to claim 2, wherein the extraction solvent is a food-grade extraction solvent.

6. A process for extracting oil from *Morinda citrifolia* seeds according to claim 2, wherein the extraction solvent is hexane.

7. A process for extracting oil from *Morinda citrifolia* seeds according to claim 1, further comprising the step of removing impurities from the *Morinda citrifolia* oil.

8. A process for extracting oil from *Morinda citrifolia* seeds according to claim 7, wherein the impurities are precipitated by addition of a precipitating agent and removed from the *Morinda citrifolia* oil by centrifuge.

9. A process for extracting oil from *Morinda citrifolia* seeds according to claim 1, further comprising the step of bleaching the *Morinda citrifolia* oil.

10. A process for extracting oil from *Morinda citrifolia* seeds according to claim 1, further comprising the step of deodorizing the *Morinda citrifolia* oil.

11. A process for extracting oil from *Morinda citrifolia* seeds according to claim 1, wherein the seeds are processed to a size between 2 mm to 20 mm.

12. A process for extracting oil from *Morinda citrifolia* seeds according to claim 1, further comprising the step of adding an antioxidant to the *Morinda citrifolia* oil.

13. A process for extracting oil from *Morinda citrifolia* seeds according to claim 12, wherein the antioxidant is selected from tocopherol acetate (vitamin E acetate), propyl gallate, TBHQ (t-butyl hydroquinone), BHT (3,5-bis(t-butyl)-4-hydroxytoluene), and French maritime pine bark extract.

14. A process for extracting oil from *Morinda citrifolia* seeds comprising the steps of:

obtaining *Morinda citrifolia* seeds that are dried to a moisture content less than 10%;

processing the seeds by cracking, flaking, or grinding to reduce their size in the range from 2 mm to 20 mm;

pressing the processed seeds to expel *Morinda citrifolia* oil;

mixing the pressed, processed seeds with a food-grade, nonpolar extraction solvent to allow *Morinda citrifolia* oil from the seeds to mix with the extraction solvent;

heating the mixture of seeds and extraction solvent to a temperature from 80° F. and 200° F. to extract *Morinda citrifolia* oil from the seeds; and removing impurities from the *Morinda citrifolia* oil.

15. A process for extracting oil from *Morinda citrifolia* seeds according to claim 14, wherein the mixture of seeds and extraction solvent is heated for a period between 30 minutes and 12 hours.

16. A process for extracting oil from *Morinda citrifolia* seeds according to claim 14, further comprising the step of removing the extraction solvent from the *Morinda citrifolia* oil by evaporation.

17. A process for extracting oil from *Morinda citrifolia* seeds according to claim 14, wherein the extraction solvent is hexane.

18. A process for extracting oil from *Morinda citrifolia* seeds according to claim 14, wherein the impurities are precipitated by addition of a precipitating agent and removed from the *Morinda citrifolia* oil by centrifuge.

19. A process for extracting oil from *Morinda citrifolia* seeds according to claim 14, further comprising the step of bleaching the *Morinda citrifolia* oil.

20. A process for extracting oil from *Morinda citrifolia* seeds according to claim 14, wherein step of bleaching the *Morinda citrifolia* oil comprises:

adding a filtering agent selected from diatomaceous earth (D.E.) and activated charcoal to the *Morinda citrifolia* oil;

heating the mixture of filtering agent and *Morinda citrifolia* oil to a temperature between 100° F. and 200° F.; and removing the filter agent by mechanical filtration.

21. A process for extracting oil from *Morinda citrifolia* seeds according to claim 14, further comprising the step of removing volatile impurities by distilling the *Morinda citrifolia* oil.

22. A process for extracting oil from *Morinda citrifolia* seeds according to claim 14, further comprising the step of removing residual water by vacuum drying the *Morinda citrifolia* oil.

23. A process for extracting oil from *Morinda citrifolia* seeds according to claim 14, further comprising the step of adding an antioxidant to the *Morinda citrifolia* oil.

24. A process for extracting oil from *Morinda citrifolia* seeds according to claim 23, wherein the antioxidant is selected from tocopherol acetate (vitamin E acetate), propyl gallate, TBHQ (t-butyl hydroquinone), BHT (3,5-bis(t-butyl)-4-hydroxytoluene), and French maritime pine bark extract.

* * * * *